US008530414B2

(12) United States Patent
Davies et al.

(10) Patent No.: US 8,530,414 B2
(45) Date of Patent: Sep. 10, 2013

(54) ANTIBODIES TO PCSK9 AND USES THEREOF

(75) Inventors: Julian Davies, La Jolla, CA (US); Ryan James Darling, Fishers, IN (US); Barrett Allan, Encinitas, CA (US)

(73) Assignee: Eli Lilly and Company, Indianapolis, IN (US)

(*) Notice: Subject to any disclaimer, the term of this patent is extended or adjusted under 35 U.S.C. 154(b) by 0 days.

(21) Appl. No.: 13/611,196

(22) Filed: Sep. 12, 2012

(65) Prior Publication Data

US 2013/0071405 A1    Mar. 21, 2013

Related U.S. Application Data

(60) Provisional application No. 61/535,625, filed on Sep. 16, 2011.

(51) Int. Cl.
| | | |
|---|---|---|
| *A61K 38/00* | (2006.01) | |
| *A61K 39/395* | (2006.01) | |
| *A61K 39/00* | (2006.01) | |
| *C12P 21/08* | (2006.01) | |
| *C07K 16/00* | (2006.01) | |

(52) U.S. Cl.
USPC ... 514/7.4; 424/130.1; 424/133.1; 424/141.1; 530/387.3; 530/388.1

(58) Field of Classification Search
None
See application file for complete search history.

(56) References Cited

U.S. PATENT DOCUMENTS

| | | | | |
|---|---|---|---|---|
| 8,030,457 | B2 * | 10/2011 | Jackson et al. | 530/388.24 |
| 8,062,640 | B2 | 11/2011 | Sleeman et al. | |
| 8,080,243 | B2 * | 12/2011 | Liang et al. | 424/130.1 |
| 8,168,762 | B2 * | 5/2012 | Jackson et al. | 530/388.24 |
| 8,188,233 | B2 * | 5/2012 | Condra et al. | 530/387.1 |
| 8,426,363 | B2 * | 4/2013 | Liang et al. | 514/7.4 |
| 2009/0142352 | A1 | 6/2009 | Jackson et al. | |
| 2009/0246192 | A1 | 10/2009 | Condra et al. | |
| 2010/0166768 | A1 | 7/2010 | Sleeman et al. | |

FOREIGN PATENT DOCUMENTS

| | | |
|---|---|---|
| WO | 01/31007 A2 | 5/2001 |
| WO | 02/14358 A2 | 2/2002 |
| WO | 2008/057457 A2 | 5/2008 |
| WO | 2008/057458 A2 | 5/2008 |
| WO | 2008/057459 A2 | 5/2008 |
| WO | 2008/063382 A2 | 5/2008 |
| WO | 2008/105797 A2 | 9/2008 |
| WO | 2008/125623 A2 | 10/2008 |
| WO | 2008/133647 A2 | 11/2008 |
| WO | 2009/026558 A1 | 2/2009 |
| WO | 2009/055783 A2 | 4/2009 |
| WO | 2009/100297 A1 | 8/2009 |
| WO | 2009/100318 A1 | 8/2009 |
| WO | 2009/131740 A2 | 10/2009 |
| WO | 2010/029513 A2 | 3/2010 |
| WO | 2010/077854 A1 | 7/2010 |
| WO | 2011/053759 A1 | 5/2011 |
| WO | 2011/072263 A1 | 6/2011 |
| WO | 2011/111007 A2 | 9/2011 |

OTHER PUBLICATIONS

Maxwell, K.N., et al., "Adenoviral-Mediated Expression of Pcsk9 in Mice Results in a Low-Density Lipoprotein Receptor Knockout Phenotype," PNAS, vol. 101, No. 18, May 4, 2004, pp. 7100-7105.
Rashid, S., et al., "Decreased Plasma Cholesterol and Hypersensitivity to Statins in Mice Lacking Pcsk9," PNAS, vol. 102, No. 15, Apr. 12, 2005, pp. 5374-5379.
Lagace, T.A., et al., "Secreted PCSK9 Decreases the Number of LDL Receptors in Hepatocytes and in Livers of Parabiotic Mice," The Journal of Clinical Investigation, vol. 116, No. 11, Nov. 2006, pp. 2995-3005.
Alborn, W.E., et al., "Serum Proprotein Convertase Subtilisin Kexin Type 9 Is Correlated Directly With Serum LDL Cholesterol," Clinical Chemistry, vol. 53, No. 10, 2007, pp. 1814-1819.
Welder, G., et al., "High-Dose Atorvastatin Causes a Rapid Sustained Increase in Human Serum PCSK9 and Disrupts Its Correlation With LDL Cholesterol," Journal of Lipid Research, vol. 51, 2010, pp. 2714-2721.
Ni, Yan G., et al., "A PCSK9-Binding Antibody That Structurally Mimics the EGF(A) Domain of LDL-Receptor Reduces LDL Cholesterol In Vivo," Journal of Lipid Research, vol. 52, No. 1, Jan. 2011, pp. 78-86.
Chan, Joyce C.Y., et al., "A Proprotein Convertase Subtilisin/Kexin Type 9 Neutralizing Antibody Reduces Serum Cholesterol in Mice and Nonhuman Primates," Proceedings of the National Academy of Sciences, National Academy of Sciences, US, vol. 106, No. 24, Jun. 16, 2009, pp. 9820-9825.
Document from WIPO Examination of related application: "Written Opinion of the International Search Authority," Date of completion of this opinion as per Form PCT/ISA/210: Date of the actual completion of the International search: Nov. 8, 2012, Date of mailing of the International search report: Nov. 23, 2012.
Document from WIPO Examination of related application: "International Search Report," Form PCT/ISA/210, Date of the actual completion of the International search: Nov. 8, 2012, Date of mailing of the International search report: Nov. 23, 2012.

* cited by examiner

*Primary Examiner* — Shulamith H Shafer
(74) *Attorney, Agent, or Firm* — Alexander Wilson

(57) ABSTRACT

The present invention relates to antibodies to proprotein convertase subtilisin/kexin type 9 (PCSK9), or antigen-binding fragments thereof, compositions comprising such PCSK9 antibodies or antigen-binding fragments, and methods of using the same for the treatment of hyperlipidemia or hypercholesterolemia.

11 Claims, No Drawings

SEQUENCE LISTING

```
<160> NUMBER OF SEQ ID NOS: 17

<210> SEQ ID NO 1
<211> LENGTH: 10
<212> TYPE: PRT
<213> ORGANISM: Artificial Sequence
<220> FEATURE:
<223> OTHER INFORMATION: Synthetic

<400> SEQUENCE: 1

Gly Phe Pro Phe Ser Lys Leu Gly Met Val
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Synthetic

<400> SEQUENCE: 2

Thr Ile Ser Ser Gly Gly Gly Tyr Thr Tyr Tyr Pro Asp Ser Val Lys
1               5                   10                  15

Gly

<210> SEQ ID NO 3
<211> LENGTH: 16
<212> TYPE: PRT
<213> ORGANISM: Artificial Sequence
<220> FEATURE:
<223> OTHER INFORMATION: Synthetic

<400> SEQUENCE: 3

Glu Gly Ile Ser Phe Gln Gly Gly Thr Tyr Thr Tyr Val Met Asp Tyr
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: Synthetic

<400> SEQUENCE: 4

Arg Ser Ser Lys Ser Leu Leu His Arg Asn Gly Ile Thr Tyr Ser Tyr
1               5                   10                  15
```

```
<210> SEQ ID NO 5
<211> LENGTH: 7
<212> TYPE: PRT
<213> ORGANISM: Artificial Sequence
<220> FEATURE:
<223> OTHER INFORMATION: Synthetic

<400> SEQUENCE: 5

Gln Leu Ser Asn Leu Ala Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic

<400> SEQUENCE: 6

Tyr Gln Asn Leu Glu Leu Pro Leu Thr
1               5

<210> SEQ ID NO 7
<211> LENGTH: 125
<212> TYPE: PRT
<213> ORGANISM: Artificial Sequence
<220> FEATURE:
<223> OTHER INFORMATION: Synthetic

<400> SEQUENCE: 7

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Pro Phe Ser Lys Leu
            20                  25                  30

Gly Met Val Trp Val Arg Gln Ala Pro Gly Lys Gly Leu Glu Trp Val
        35                  40                  45

Ser Thr Ile Ser Ser Gly Gly Gly Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ile Ser Phe Gln Gly Gly Thr Tyr Thr Tyr Val Met
            100                 105                 110

Asp Tyr Trp Gly Gln Gly Thr Leu Val Thr Val Ser Ser
        115                 120                 125

<210> SEQ ID NO 8
<211> LENGTH: 112
<212> TYPE: PRT
<213> ORGANISM: Artificial Sequence
<220> FEATURE:
<223> OTHER INFORMATION: Synthetic

<400> SEQUENCE: 8

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Arg
            20                  25                  30

Asn Gly Ile Thr Tyr Ser Tyr Trp Tyr Leu Gln Lys Pro Gly Gln Ser
        35                  40                  45

Pro Gln Leu Leu Ile Tyr Gln Leu Ser Asn Leu Ala Ser Gly Val Pro
```

```
                 50                  55                  60
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Tyr Gln Asn
                 85                  90                  95

Leu Glu Leu Pro Leu Thr Phe Gly Gln Gly Thr Lys Val Glu Ile Lys
            100                 105                 110

<210> SEQ ID NO 9
<211> LENGTH: 451
<212> TYPE: PRT
<213> ORGANISM: Artificial Sequence
<220> FEATURE:
<223> OTHER INFORMATION: Synthetic

<400> SEQUENCE: 9

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Pro Phe Ser Lys Leu
                 20                  25                  30

Gly Met Val Trp Val Arg Gln Ala Pro Gly Lys Gly Leu Glu Trp Val
             35                  40                  45

Ser Thr Ile Ser Ser Gly Gly Gly Tyr Thr Tyr Tyr Pro Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Gly Ile Ser Phe Gln Gly Gly Thr Tyr Thr Tyr Val Met
            100                 105                 110

Asp Tyr Trp Gly Gln Gly Thr Leu Val Thr Val Ser Ser Ala Ser Thr
            115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Lys Thr Tyr Thr Cys
            195                 200                 205

Asn Val Asp His Lys Pro Ser Asn Thr Lys Val Asp Lys Arg Val Glu
210                 215                 220

Ser Lys Tyr Gly Pro Pro Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
            275                 280                 285

Val His Asn Ala Lys Thr Lys Pro Arg Glu Glu Gln Phe Asn Ser Thr
            290                 295                 300

Tyr Arg Val Val Ser Val Leu Thr Val Leu His Gln Asp Trp Leu Asn
305                 310                 315                 320
```

Gly Lys Glu Tyr Lys Cys Lys Val Ser Asn Lys Gly Leu Pro Ser Ser
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Met Thr Lys Asn Gln Val
            355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Tyr Lys Thr Thr Pro
385                 390                 395                 400

Pro Val Leu Asp Ser Asp Gly Ser Phe Phe Leu Tyr Ser Arg Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Leu Gly
   450

<210> SEQ ID NO 10
<211> LENGTH: 219
<212> TYPE: PRT
<213> ORGANISM: Artificial Sequence
<220> FEATURE:
<223> OTHER INFORMATION: Synthetic

<400> SEQUENCE: 10

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Arg
            20                  25                  30

Asn Gly Ile Thr Tyr Ser Tyr Trp Tyr Leu Gln Lys Pro Gly Gln Ser
            35                  40                  45

Pro Gln Leu Leu Ile Tyr Gln Leu Ser Asn Leu Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Tyr Gln Asn
                85                  90                  95

Leu Glu Leu Pro Leu Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 11
<211> LENGTH: 1356
<212> TYPE: DNA
<213> ORGANISM: Artificial Sequence
<220> FEATURE:
<223> OTHER INFORMATION: Synthetic

<400> SEQUENCE: 11

```
gaggtgcagc tggtggagtc tgggggaggc ttggtaaagc ctgggggtc  cctgagactc      60
tcctgtgcag cctctggatt cccgttcagt aagctcggca tggtttgggt ccgccaggct     120
ccagggaagg ggctggagtg ggtctcaacc attagtagtg gtggtggtta cacatactat     180
ccagacagtg tgaaggggcg gttcaccatc tccagagaca atgccaagaa ctcactgtat     240
ctgcaaatga acagcctgag agccgaggac acggccgtat attactgtgc gagagaagga     300
attagctttc agggtggcac ctacacttat gttatggact actggggcca gggcaccctg     360
gtcaccgtct cctcagcctc caccaagggc ccatcggtct tccccgctag cccctgctcc     420
aggagcacct ccgagagcac agccgccctg gctgcctgg tcaaggacta cttccccgaa     480
ccggtgacgg tgtcgtggaa ctcaggcgcc ctgaccagcg gcgtgcacac cttcccggct     540
gtcctacagt cctcaggact ctactccctc agcagcgtgg tgaccgtgcc ctccagcagc     600
ttgggcacga gacctacac  ctgcaacgta gatcacaagc ccagcaacac caaggtggac     660
aagagagttg agtccaaata tggtccccca tgcccaccct gcccagcacc tgaggccgcc     720
gggggaccat cagtcttcct gttcccccca aaacccaagg acactctcat gatctcccgg     780
acccctgagg tcacgtgcgt ggtggtggac gtgagccagg aagaccccga ggtccagttc     840
aactggtacg tggatggcgt ggaggtgcat aatgccaaga caaagccgcg ggaggagcag     900
ttcaacagca cgtaccgtgt ggtcagcgtc ctcaccgtcc tgcaccagga ctggctgaac     960
ggcaaggagt acaagtgcaa ggtctccaac aaaggcctcc cgtcctccat cgagaaaacc    1020
atctccaaag ccaaagggca gccccgagag ccacaggtgt acaccctgcc cccatcccag    1080
gaggagatga ccaagaacca ggtcagcctg acctgcctgg tcaaaggctt ctaccccagc    1140
gacatcgccg tggagtggga aagcaatggg cagccggaga caactacaa  gaccacgcct    1200
cccgtgctgg actccgacgg ctccttcttc ctctacagca ggctaaccgt ggacaagagc    1260
aggtggcagg agggaatgt  cttctcatgc tccgtgatgc atgaggctct gcacaaccac    1320
tacacacaga gagcctctc  cctgtctctg ggttga                              1356
```

<210> SEQ ID NO 12
<211> LENGTH: 660
<212> TYPE: DNA
<213> ORGANISM: Artificial Sequence
<220> FEATURE:
<223> OTHER INFORMATION: Synthetic

<400> SEQUENCE: 12

```
gatattgtga tgactcagtc tccactctcc ctgcccgtca cccctggaga gccggcctcc      60
atctcctgca ggtctagtaa gagtctctta catcgtaatg gcatcactta ttcgtattgg     120
tacctgcaga agccagggca gtctccacag ctcctgatct atcagctgtc caaccttgcc     180
tcaggagtcc cagacaggtt cagtggcagt gggtcaggca ctgatttcac actgaaaatc     240
agcagggtgg aggctgagga tgttggagtt tattactgct atcaaaatct agaacttccg     300
ctcacgttcg gccagggcac caaggtggaa atcaaacgga ctgtggctgc accatctgtc     360
ttcatcttcc cgccatctga tgagcagttg aaatctggaa ctgcctctgt tgtgtgcctg     420
```

```
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgctaa    660
```

<210> SEQ ID NO 13
<211> LENGTH: 672
<212> TYPE: PRT
<213> ORGANISM: Artificial Sequence
<220> FEATURE:
<223> OTHER INFORMATION: Synthetic

<400> SEQUENCE: 13

```
Arg Ala Gln Glu Asp Glu Asp Gly Asp Tyr Glu Glu Leu Val Leu Ala
1               5                   10                  15

Leu Arg Ser Glu Glu Asp Gly Leu Ala Glu Ala Pro Glu His Gly Thr
            20                  25                  30

Thr Ala Thr Phe His Arg Cys Ala Lys Asp Pro Trp Arg Leu Pro Gly
        35                  40                  45

Thr Tyr Val Val Leu Lys Glu Glu Thr His Leu Ser Gln Ser Glu
    50                  55                  60

Arg Thr Ala Arg Arg Leu Gln Ala Gln Ala Ala Arg Arg Gly Tyr Leu
65                  70                  75                  80

Thr Lys Ile Leu His Val Phe His Gly Leu Leu Pro Gly Phe Leu Val
                85                  90                  95

Lys Met Ser Gly Asp Leu Leu Glu Leu Ala Leu Lys Leu Pro His Val
            100                 105                 110

Asp Tyr Ile Glu Glu Asp Ser Ser Val Phe Ala Gln Ser Ile Pro Trp
        115                 120                 125

Asn Leu Glu Arg Ile Thr Pro Pro Arg Tyr Arg Ala Asp Glu Tyr Gln
    130                 135                 140

Pro Pro Asp Gly Gly Ser Leu Val Glu Val Tyr Leu Leu Asp Thr Ser
145                 150                 155                 160

Ile Gln Ser Asp His Arg Glu Ile Glu Gly Arg Val Met Val Thr Asp
                165                 170                 175

Phe Glu Asn Val Pro Glu Glu Asp Gly Thr Arg Phe His Arg Gln Ala
            180                 185                 190

Ser Lys Cys Asp Ser His Gly Thr His Leu Ala Gly Val Val Ser Gly
        195                 200                 205

Arg Asp Ala Gly Val Ala Lys Gly Ala Ser Met Arg Ser Leu Arg Val
    210                 215                 220

Leu Asn Cys Gln Gly Lys Gly Thr Val Ser Gly Thr Leu Ile Gly Leu
225                 230                 235                 240

Glu Phe Ile Arg Lys Ser Gln Leu Val Gln Pro Val Gly Pro Leu Val
                245                 250                 255

Val Leu Leu Pro Leu Ala Gly Gly Tyr Ser Arg Val Leu Asn Ala Ala
            260                 265                 270

Cys Gln Arg Leu Ala Arg Ala Gly Val Val Leu Val Thr Ala Ala Gly
        275                 280                 285

Asn Phe Arg Asp Asp Ala Cys Leu Tyr Ser Pro Ala Ser Ala Pro Glu
    290                 295                 300

Val Ile Thr Val Gly Ala Thr Asn Ala Gln Asp Gln Pro Val Thr Leu
305                 310                 315                 320

Gly Thr Leu Gly Thr Asn Phe Gly Arg Cys Val Asp Leu Phe Ala Pro
                325                 330                 335
```

```
Gly Glu Asp Ile Ile Gly Ala Ser Ser Asp Cys Ser Thr Cys Phe Val
            340                 345                 350

Ser Gln Ser Gly Thr Ser Gln Ala Ala His Val Ala Gly Ile Ala
        355                 360                 365

Ala Met Met Leu Ser Ala Glu Pro Glu Leu Thr Leu Ala Glu Leu Arg
370                 375                 380

Gln Arg Leu Ile His Phe Ser Ala Lys Asp Val Ile Asn Glu Ala Trp
385                 390                 395                 400

Phe Pro Glu Asp Gln Arg Val Leu Thr Pro Asn Leu Val Ala Ala Leu
                405                 410                 415

Pro Pro Ser Thr His Gly Ala Gly Trp Gln Leu Phe Cys Arg Thr Val
                420                 425                 430

Trp Ser Ala His Ser Gly Pro Thr Arg Met Ala Thr Ala Val Ala Arg
                435                 440                 445

Cys Ala Pro Asp Glu Glu Leu Leu Ser Cys Ser Ser Phe Ser Arg Ser
            450                 455                 460

Gly Lys Arg Arg Gly Glu Arg Met Glu Ala Gln Gly Gly Lys Leu Val
465                 470                 475                 480

Cys Arg Ala His Asn Ala Phe Gly Gly Glu Gly Val Tyr Ala Ile Ala
                485                 490                 495

Arg Cys Cys Leu Leu Pro Gln Ala Asn Cys Ser Val His Thr Ala Pro
            500                 505                 510

Pro Ala Glu Ala Ser Met Gly Thr Arg Val His Cys His Gln Gln Gly
            515                 520                 525

His Val Leu Thr Gly Cys Ser Ser His Trp Glu Val Glu Asp Leu Gly
        530                 535                 540

Thr His Lys Pro Pro Val Leu Arg Pro Arg Gly Gln Pro Asn Gln Cys
545                 550                 555                 560

Val Gly His Arg Glu Ala Ser Ile His Ala Ser Cys Cys His Ala Pro
                565                 570                 575

Gly Leu Glu Cys Lys Val Lys Glu His Gly Ile Pro Ala Pro Gln Glu
            580                 585                 590

Gln Val Thr Val Ala Cys Glu Glu Gly Trp Thr Leu Thr Gly Cys Ser
        595                 600                 605

Ala Leu Pro Gly Thr Ser His Val Leu Gly Ala Tyr Ala Val Asp Asn
        610                 615                 620

Thr Cys Val Val Arg Ser Arg Asp Val Ser Thr Thr Gly Ser Thr Ser
625                 630                 635                 640

Glu Gly Ala Val Thr Ala Val Ala Ile Cys Cys Arg Ser Arg His Leu
                645                 650                 655

Ala Gln Ala Ser Gln Glu Leu Gln Asp Val His His His His His His
            660                 665                 670

<210> SEQ ID NO 14
<211> LENGTH: 22
<212> TYPE: PRT
<213> ORGANISM: Artificial Sequence
<220> FEATURE:
<223> OTHER INFORMATION: Synthetic

<400> SEQUENCE: 14

Arg Ile Thr Pro Pro Arg Tyr Arg Ala Asp Glu Tyr Gln Pro Pro Asp
1               5                   10                  15

Gly Gly Ser Leu Val Glu
            20
```

```
<210> SEQ ID NO 15
<211> LENGTH: 16
<212> TYPE: PRT
<213> ORGANISM: Artificial Sequence
<220> FEATURE:
<223> OTHER INFORMATION: Synthetic

<400> SEQUENCE: 15

Tyr Arg Ala Asp Glu Tyr Gln Pro Pro Asp Gly Gly Ser Leu Val Glu
1               5                   10                  15

<210> SEQ ID NO 16
<211> LENGTH: 12
<212> TYPE: PRT
<213> ORGANISM: Artificial Sequence
<220> FEATURE:
<223> OTHER INFORMATION: Synthetic

<400> SEQUENCE: 16

Pro Pro Arg Tyr Arg Ala Asp Glu Tyr Gln Pro Pro
1               5                   10

<210> SEQ ID NO 17
<211> LENGTH: 376
<212> TYPE: PRT
<213> ORGANISM: Artificial Sequence
<220> FEATURE:
<223> OTHER INFORMATION: Synthetic

<400> SEQUENCE: 17

Gln Glu Asp Glu Asp Gly Asp Tyr Glu Glu Leu Val Leu Ala Leu Arg
1               5                   10                  15

Ser Glu Glu Asp Gly Leu Ala Glu Ala Pro Glu His Gly Thr Thr Ala
            20                  25                  30

Thr Phe His Arg Cys Ala Lys Asp Pro Trp Arg Leu Pro Gly Thr Tyr
        35                  40                  45

Val Val Val Leu Lys Glu Glu Thr His Leu Ser Gln Ser Glu Arg Thr
    50                  55                  60

Ala Arg Arg Leu Gln Ala Gln Ala Ala Arg Arg Gly Tyr Leu Thr Lys
65                  70                  75                  80

Ile Leu His Val Phe His Gly Leu Leu Pro Gly Phe Leu Val Lys Met
                85                  90                  95

Ser Gly Asp Leu Leu Glu Leu Ala Leu Lys Leu Pro His Val Asp Tyr
            100                 105                 110

Ile Glu Glu Asp Ser Ser Val Phe Ala Gln Ser Ile Pro Trp Asn Leu
        115                 120                 125

Glu Arg Ile Thr Pro Pro Arg Tyr Arg Ala Asp Glu Tyr Gln Pro Pro
    130                 135                 140

Asp Gly Gly Ser Leu Val Glu Val Tyr Leu Leu Asp Thr Ser Ile Gln
145                 150                 155                 160

Ser Asp His Arg Glu Ile Glu Gly Arg Val Met Val Thr Asp Phe Glu
                165                 170                 175

Asn Val Pro Glu Glu Asp Gly Thr Arg Phe His Arg Gln Ala Ser Lys
            180                 185                 190

Cys Asp Ser His Gly Thr His Leu Ala Gly Val Val Ser Gly Arg Asp
        195                 200                 205

Ala Gly Val Ala Lys Gly Ala Ser Met Arg Ser Leu Arg Val Leu Asn
    210                 215                 220

Cys Gln Gly Lys Gly Thr Val Ser Gly Thr Leu Ile Gly Leu Glu Phe
225                 230                 235                 240
```

```
Ile Arg Lys Ser Gln Leu Val Gln Pro Val Gly Pro Leu Val Val Leu
            245                 250                 255

Leu Pro Leu Ala Gly Gly Tyr Ser Arg Val Leu Asn Ala Ala Cys Gln
            260                 265                 270

Arg Leu Ala Arg Ala Gly Val Val Leu Val Thr Ala Ala Gly Asn Phe
            275                 280                 285

Arg Asp Asp Ala Cys Leu Tyr Ser Pro Ala Ser Ala Pro Glu Val Ile
            290                 295                 300

Thr Val Gly Ala Thr Asn Ala Gln Asp Gln Pro Val Thr Leu Gly Thr
305                 310                 315                 320

Leu Gly Thr Asn Phe Gly Arg Cys Val Asp Leu Phe Ala Pro Gly Glu
                325                 330                 335

Asp Ile Ile Gly Ala Ser Ser Asp Cys Ser Thr Cys Phe Val Ser Gln
                340                 345                 350

Ser Gly Thr Ser Gln Ala Ala Ala His Val Ala Gly Ile Ala Ala Met
            355                 360                 365

Met Leu Ser Ala Glu Pro Glu Leu
    370                 375
```

US 8,530,414 B2

ANTIBODIES TO PCSK9 AND USES THEREOF

The present invention is in the field of medicine. Particularly, the present invention relates to antibodies to proprotein convertase subtilisin/kexin type 9 (PCSK9), compositions comprising such PCSK9 antibodies, and methods of using PCSK9 antibodies for the treatment of hyperlipidemia or hypercholesterolemia.

Proprotein convertase subtilisin/kexin type 9 (PCSK9) is a secreted serine protease, generated primarily in the liver, that regulates plasma concentrations of low density lipoprotein cholesterol (LDL-C). Secreted PCSK9 binds to and internalizes with the LDL receptor (LDLR) located on the surface of hepatocytes. LDLR functions to clear LDL-C from plasma by binding and transporting LDL particles to lysosomes for degradation. Once the LDL particle is delivered for degradation, the LDLR recycles to the hepatocyte cell surface to bind and clear additional LDL-C from the plasma. PCSK9 regulates plasma LDL-C by directing internalized LDLR for degradation rather than recycling to the cell surface, thus reducing LDL-C clearance. Studies in rodents in which PCSK9 is deficient or over-expressed have now confirmed that PCSK9 controls circulating LDL levels by modulating the levels of LDLR. The observation that circulating PCSK9 participates in the degradation of hepatic LDLR suggests that antibody neutralization of PCSK9 is a viable therapeutic approach for lowering of LDL-C. Further, it has been reported that statin drugs, the current standard of care for lowering LDL-C, may actually increase the expression and serum levels of PCSK9. Thus, a PCSK9 antibody also has the potential to reduce LDL-C in a manner synergistic with statin therapy.

PCSK9 antibodies and their effects on lowering plasma LDL-C are known in the art. For example, US2009/0246192, US2009/0142352, US2010/0166768, and WO2010/029513 disclose such PCSK9 antibodies and their use. However, to date, no antibody targeting PCSK9 has been approved for therapeutic use. Thus, there remains a need for alternative PCSK9 antibodies. In particular, there remains a need for alternative PCSK9 antibodies which reduce LDL-C with high potency. More particular still, there remains a need for alternative PCSK9 antibodies which reduce LDL-C with high potency and which provide sustained duration of action (e.g. sustained suppression of LDL-C levels). Such antibodies would preferably also possess good physical-chemical properties to facilitate development, manufacturing, or formulation.

The present invention provides an antibody, or antigen-binding fragment thereof, comprising a heavy chain variable region (HCVR) and a light chain variable region (LCVR), wherein the HCVR comprises the complementarity determining regions (CDRs) HCDR1, HCDR2 and HCDR3 and the LCVR comprises the CDRs LCDR1, LCDR2 and LCDR3, wherein the amino acid sequence of HCDR1 is given by SEQ ID NO: 1, the amino acid sequence of HCDR2 is given by SEQ ID NO: 2, the amino acid sequence of HCDR3 is given by SEQ ID NO: 3, the amino acid sequence of LCDR1 is given by SEQ ID NO: 4, the amino acid sequence of LCDR2 is given by SEQ ID NO: 5, and the amino acid sequence of LCDR3 is given by SEQ ID NO: 6, wherein said antibody or antigen-binding fragment thereof binds to human PCSK9. In an embodiment, the present invention provides an antibody, or antigen-binding fragment thereof, comprising a heavy chain variable region (HCVR) and a light chain variable region (LCVR), wherein the amino acid sequence of the HCVR is given by SEQ ID NO: 7 and the amino acid sequence of the LCVR is given by SEQ ID NO: 8, wherein said antibody or antigen-binding fragment thereof binds to human PCSK9. In another embodiment, the present invention provide an antibody, or antigen-binding fragment thereof, comprising two heavy chain variable regions (HCVRs) and two light chain variable regions wherein the amino acid sequence of each HCVR is given by SEQ ID NO: 7 and the amino acid sequence of each LCVR is given by SEQ ID NO: 8.

In another particular embodiment, the present invention provides an antibody, or an antigen-binding fragment thereof, comprising a heavy chain (HC) and a light chain (LC), wherein the amino acid sequence of the HC is given by SEQ ID NO: 9 and the amino acid sequence of the LC is given by SEQ ID NO: 10. In an even more particular embodiment, the present invention provides an antibody comprising two heavy chains (HCs) and two light chains (LCs) wherein the amino acid sequence of each HC is given by SEQ ID NO: 9 and the amino acid sequence of each LC is given by SEQ ID NO: 10. In a most particular embodiment, the present invention provides an antibody that consists of two HCs and two LCs, wherein the amino acid sequence of each HC is given by SEQ ID NO: 9 and the amino acid sequence of each LC is given by SEQ ID NO: 10.

The present invention further provides pharmaceutical compositions comprising an antibody or antigen-binding fragment of the present invention and one or more pharmaceutically acceptable carriers, diluents or excipients. More particularly, the pharmaceutical compositions of the present invention further comprise one or more additional therapeutic agents.

In addition, the present invention provides a method of treating hyperlipidemia or hypercholesterolemia comprising administering to a patient in need thereof, an effective amount of an antibody or antigen-binding fragment of the present invention. The present invention also provides the antibody or an antigen binding fragment thereof of the present invention for use in therapy. More particularly, the present invention provides the antibody or an antigen binding fragment thereof of the present invention for use in the treatment of hyperlipidemia or hypercholesterolemia. In addition, the present invention provides the use of the antibody or an antigen binding fragment thereof of the present invention in the manufacture of a medicament for the treatment of hyperlipidemia or hypercholesterolemia.

The present invention also relates to nucleic acid molecules and expression vectors encoding the antibody or antigen-binding fragment of the present invention. Further, the present invention provides an antibody prepared according to a process, wherein said process comprises (a) cultivating a host cell comprising a first polynucleotide sequence encoding the polypeptide sequence given by SEQ ID NO: 9 and a second polynucleotide sequence encoding a second polypeptide sequence given by SEQ ID NO:10, under conditions such that said polypeptide sequences are expressed; and (b) recovering from said host cell an antibody comprising a heavy chain and a light chain, wherein the polypeptide sequence of said heavy chain is given by SEQ ID NO:9 and the polypeptide sequence of said light chain is given by SEQ ID NO:10. More particularly, the antibody produced by the afore-mentioned process comprises two heavy chains and two light chains, wherein the polypeptide sequence of each heavy chain is given by SEQ ID NO:9 and the polypeptide sequence of each light chain is given by SEQ ID NO:10.

A full-length antibody is an immunoglobulin molecule comprising 2 heavy (H) chains and 2 light (L) chains interconnected by disulfide bonds. The amino terminal portion of each chain includes a variable region of about 100-110 amino acids primarily responsible for antigen recognition via the complementarity determining regions (CDRs) contained therein. The carboxy-terminal portion of each chain defines a constant region primarily responsible for effector function. Light chains are classified as kappa or lambda, which are each characterized by a particular constant region as known in the art. Heavy chains are classified as gamma, mu, alpha, delta, or epsilon, and define the isotype of an antibody as IgG, IgM, IgA, IgD, or IgE, respectively. IgG antibodies can be further divided into subclasses, e.g., IgG1, IgG2, IgG3, IgG4. Each heavy chain type is also characterized by a particular constant region with a sequence well known in the art. "Antigen-binding fragment", as used herein, refers to Fab fragments, Fab' fragments, F(ab')$_2$ fragments, and single chain Fv fragments that bind to human PCSK9. The term "bind (or 'binds') to human PCSK9", as used herein, refers to interaction with an epitope on human PCSK9 given by the amino acid sequence of SEQ ID NO: 14. The term "epitope" as used herein refers to discrete, three-dimensional sites on an antigen that are recognized by the antibodies or antigen-binding fragments of the invention.

The CDRs are interspersed with regions that are more conserved, termed framework regions ("FR"). Each light chain variable region (LCVR) and heavy chain variable region (HCVR) is composed of 3 CDRs and 4 FRs, arranged from amino-terminus to carboxy-terminus in the following order: FR1, CDR1, FR2, CDR2, FR3, CDR3, FR4. The 3 CDRs of the light chain are referred to as "LCDR1, LCDR2, and LCDR3" and the 3 CDRs of the heavy chain are referred to as "HCDR1, HCDR2, and HCDR3." The CDRs contain most of the residues which form specific interactions with the antigen. The numbering and positioning of CDR amino acid residues within the LCVR and HCVR regions of the antibodies or antigen-binding fragments of the present invention may be determined in accordance with the well-known Kabat numbering convention (LCDR 1-3, HCDR2-3), or in accordance with Kabat plus Chothia (HCDR1).

Methods for producing and purifying antibodies and antigen-binding fragments are well known in the art and can be found, for example, in Harlow and Lane (1988) *Antibodies, A Laboratory Manual*, Cold Spring Harbor Laboratory Press, Cold Spring Harbor, N.Y., chapters 5-8 and 15. For example, mice can be immunized with human PCSK9, or fragments thereof, and the resulting antibodies can then be recovered, purified, and the amino acid sequences determined using conventional methods well known in the art. Antigen-binding fragments can also be prepared by conventional methods. The antibody or antigen binding fragments of the present invention are engineered to contain one or more human framework regions surrounding CDRs derived from a non-human antibody. Human framework germline sequences can be obtained from ImMunoGeneTics (IMGT) via their website http://imgt.cines.fr, or from *The Immunoglobulin Facts Book* by Marie-Paule Lefranc and Gerard Lefranc, Academic Press, 2001, ISBN 012441351. Particular, germline light chain frameworks for use in the antibody or antigen binding fragments of the present invention include A3 and O$_2$. Particular germline heavy chain framework regions for use in the antibody or antigen binding fragments of the present invention include VH3-21 and VH3-23.

The engineered antibodies or antigen binding fragments of the present invention may be prepared and purified using known methods. For example, cDNA sequences encoding a heavy chain (for example, the amino acid sequence given by SEQ ID NO: 9) and a light chain (for example, the amino acid sequence given by SEQ ID NO: 10) may be cloned and engineered into a GS (glutamine synthetase) expression vector. The engineered immunoglobulin expression vector may then be stably transfected in CHO cells. As one of skill in the art will appreciate, mammalian expression of antibodies will result in glycosylation, typically at highly conserved N-glycosylation sites in the Fc region. Stable clones may be verified for expression of an antibody specifically binding to human PCSK9. Positive clones may be expanded into serum-free culture medium for antibody production in bioreactors. Media, into which an antibody has been secreted, may be purified by conventional techniques. For example, the medium may be conveniently applied to a Protein A or G Sepharose FF column that has been equilibrated with a compatible buffer, such as phosphate buffered saline. The column is washed to remove nonspecific binding components. The bound antibody is eluted, for example, by pH gradient and antibody fractions are detected, such as by SDS-PAGE, and then pooled. The antibody may be concentrated and/or sterile filtered using common techniques. Soluble aggregate and multimers may be effectively removed by common techniques, including size exclusion, hydrophobic interaction, ion exchange, or hydroxyapatite chromatography. The product may be immediately frozen, for example at −70° C., or may be lyophilized.

The antibodies of the present invention are monoclonal antibodies. "Monoclonal antibody" or "mAb", as used herein, refers to an antibody that is derived from a single copy or clone including, for example, any eukaryotic, prokaryotic, or phage clone, and not the method by which it is produced. Monoclonal antibodies and antigen-binding fragments thereof can be produced, for example, by hybridoma technologies, recombinant technologies, phage display technologies, synthetic technologies, e.g., CDR-grafting, or combinations of such or other technologies known in the art.

In another embodiment of the present invention, the antibody or antigen-binding fragment thereof, or the nucleic acid encoding the same, is provided in isolated form. As used herein, the term "isolated" refers to a protein, peptide or nucleic acid which is free or substantially free from other macromolecular species found in a cellular environment. "Substantially free", as used herein, means the protein, peptide or nucleic acid of interest comprises more than 80% (on a molar basis) of the macromolecular species present, preferably more than 90% and more preferably more than 95%.

The antibodies or antigen-binding fragments of the present invention can be used in the treatment of patients. The term "treating" (or "treat" or "treatment") refers to slowing, interrupting, arresting, alleviating, stopping, reducing, or reversing the progression or severity of an existing symptom, disorder, condition, or disease. "Patient", as used herein, refers to a human or non-human mammal, but preferably refers to a human. As used herein the term "effective amount" refers to the amount or dose of an antibody or antigen-binding fragment of the present invention which, upon single or multiple dose administration to the patient, provides the desired effect in the patient under treatment. An effective amount can be readily determined by the attending diagnostician, as one skilled in the art, by considering a number of factors such as the species of mammal; its size, age, and general health; the specific disease involved; the degree or severity of the disease; the response of the individual patient; the particular antibody administered; the mode of administration; the bioavailability characteristics of the preparation administered; the dose regimen selected; and the use of any concomitant medications.

The antibodies or antigen-binding fragments of the present invention, or pharmaceutical compositions comprising the same, may be administered by parenteral routes (e.g., subcutaneous, intravenous, intraperitoneal, intramuscular, or transdermal). Pharmaceutical compositions of the present invention can be prepared by methods well known in the art (e.g., *Remington: The Science and Practice of Pharmacy*, 19th ed. (1995), A. Gennaro et al., Mack Publishing Co.) and comprise an antibody, or antigen-binding fragment thereof as disclosed herein, and one or more pharmaceutically acceptable carriers, diluents, or excipients. For example, an antibody or antigen-binding fragment of the present invention can be formulated with agents such as sodium citrate, citric acid, polysorbate 80, and sucrose and the resulting composition may then be lyophilized and stored at 2° C.-8° C. The lyophilized composition may then be reconstituted with sterile water for injection prior to administration.

The following Examples further illustrate the invention, however, it is understood that the Examples are set forth by way of illustration and not limitation, and that various modifications may be made by one of ordinary skill in the art.

EXAMPLE 1

Engineered PCSK9 Antibody

A murine host is immunized with a peptide comprising a C-terminal truncated fragment of human PCSK9 (SEQ ID NO: 17) and a PCSK9 binding IgG antibody is isolated and cloned using standard methods. The CDRs of the isolated murine Fab are randomized by mutagenesis and resulting antibodies screened for affinity to human PCSK9. Affinity enhancing mutations are combined and the optimized CDRs are engineered onto human VH3-21 and A3 heavy and light chain frameworks, respectively. To further optimize the biophysical properties of the humanized antibody, targeted replacements of aromatic and hydrophobic amino acids within the CDR sequences are made. Randomized CDR libraries are also screened for additional affinity enhancing mutations. Beneficial CDR mutations are randomly combined and expressed, and resulting antibodies screened for affinity to human PCSK9. A full length humanized and optimized PCSK9 antibody having the following amino acid sequences is obtained:

| mAb Fragment | Amino acid sequence |
|---|---|
| HCDR1 | SEQ ID NO: 1 |
| HCDR2 | SEQ ID NO: 2 |
| HCDR3 | SEQ ID NO: 3 |
| HCVR | SEQ ID NO: 7 |
| HC | SEQ ID NO: 9 |
| LCDR1 | SEQ ID NO: 4 |
| LCDR2 | SEQ ID NO: 5 |
| LCDR3 | SEQ ID NO: 6 |
| LCVR | SEQ ID NO: 8 |
| LC | SEQ ID NO: 10 |

The corresponding cDNA sequences encoding the heavy and light chain amino acid sequences of SEQ ID NO: 9 and SEQ ID NO: 10, respectively, are as follows:

| mAb Fragment | cDNA sequence encoding |
|---|---|
| HC | SEQ ID NO: 11 |
| LC | SEQ ID NO: 12 |

EXAMPLE 2

Expression of Engineered PCSK9 Antibody

The engineered PCSK9 antibody of Example 1 may be expressed in a stably transfected CHO cell line. A glutamine synthetase (GS) expression vector containing the cDNA of SEQ ID NO: 11 (encoding the heavy chain amino acid sequence of SEQ ID NO: 9) and SEQ ID NO: 12 (encoding the light chain amino acid sequence of SEQ ID NO: 10) is used to transfect the Chinese hamster cell line, CHOK1SV (Lonza Biologics PLC, Slough, United Kingdom) by electroporation. The expression vector encodes an SV Early (Simian Virus 40E) promoter and the gene for GS. Expression of GS allows for the biochemical synthesis of glutamine, an amino acid required by the CHOK1SV cells. Post-transfection, cells undergo bulk selection with 50 µM L-methionine sulfoximine (MSX). The inhibition of GS by MSX is utilized to increase the stringency of selection. Cells with integration of the expression vector cDNA into transcriptionally active regions of the host cell genome can be selected against CHOK1SV wild type cells, which express an endogenous level of GS. Bulk culture is subjected to single-cell cloning using Fluorescence-Activated Cell Sorting (FACS) technology and the clonal cell lines are expanded and screened for expression of the engineered PCSK9 antibody of Example 1.

EXAMPLE 3

Epitope Binding

The PCSK9 binding epitope of the murine IgG (from which the engineered PCSK9 antibody of Example 1 was derived) is determined by epitope extraction and hydrogen/deuterium exchange mass spectrometry and narrowed to a region within the linear amino acid sequence 160-181 of the catalytic domain of human PCSK9 (amino acid numbering based on full length human PCSK9 sequence, including the twenty-eight amino acid signal peptide.) The interaction of the engineered antibody of Example 1 with this epitope in the catalytic domain of human PCSK9 is confirmed by an evaluation of its binding to synthetic peptides corresponding to residues 160-181 (Table 1). The engineered antibody of Example 1 binds peptide 160-181 with higher affinity than intact human PCSK9, the difference being driven by a faster association rate ($k_{on}$). The dissociation rate ($k_{off}$) is within 2-fold of intact PCSK9, suggesting that the strength of the interactions (after binding has occurred) are similar. Furthermore, the data suggests that nearly all the binding determinants are contained within this linear region of PCSK9. Binding of the engineered antibody of Example 1 to peptide 166-181 is significantly weaker than peptide 160-181, demonstrating the role of an amino acid (or multiple amino acids) within the 160-165 region. Binding of the engineered antibody of Example 1 to peptide 163-174 was significantly stronger than 166-181, suggesting contribution from residues 163-165 as well.

TABLE 1

Binding kinetics and affinity of the antibody of
Example 1 for peptides corresponding to sequences of
the catalytic domain of human PCSK9

| PCSK9 Fragment | Sequence | $k_{on}$ (1/Ms) | $k_{off}$ (1/s) | $K_D$ (nM) |
|---|---|---|---|---|
| mature hPCSK9 C-term His* | (SEQ ID NO: 13) | 8.67E+04 | 1.50E-04 | 1.8 |
| hPCSK9 160-181** | RITPPRYRADEYQPPDGGSLVE (SEQ ID NO: 14) | 1.45E+06 | 2.42E-04 | 0.17 |
| hPCSK9 166-181** | YRADEYQPPDGGSLVE (SEQ ID NO: 15) | 4.58E+06 | 1.56E-01 | 34 |
| hPCSK9 163-174** | PPRYRADEYQPP (SEQ ID NO: 16) | 2.75E+06 | 8.31E-03 | 3.0 |

*The hPCSK9 used is the mature form which lacks the twenty-eight amino acid signal peptide and which contains a C-terminal His tag.
**Amino acid numbering assigned in reference to complete human PCSK9, including the twenty-eight amino acid signal peptide

EXAMPLE 4

Binding Kinetics and Affinity

A surface plasmon resonance (SPR) assay as well known in the art is used to assess the binding kinetics and affinity of a test PCSK9 antibody to human, cynomolgus monkey, mouse, rat, and rabbit PCSK9. Under physiological buffer conditions (ionic strength and pH) and temperature (37° C.), the engineered antibody of Example 1 binds to human PCSK9 with an average association rate ($k_{on}$) of $1.2 \times 10^5$ M$^{-1}$s$^{-1}$ and an average dissociation rate ($k_{off}$) of $1.2 \times 10^{-3}$ s$^{-1}$. The average $K_D$ for human PCSK9 binding for the engineered antibody of Example 1 was determined to be about 11 nM. The engineered antibody of Example 1 binds to cynomolgus PCSK9 with an average association rate ($k_{on}$) of $1.1 \times 10^5$ M$^{-1}$s$^{-1}$ and an average dissociation rate ($k_{off}$) of $2.5 \times 10^{-3}$ s$^{-1}$, resulting in a $K_D$ for cynomolgus PCSK9 binding of about 25 nM. Table 2 below shows a summary of additional results obtained with the engineered PCSK9 antibody of Example 1 using mouse, rat and rabbit PCSK9. These data indicate that the engineered PCSK9 antibody of Example 1 binds with nanomolar affinity to both human and cynomolgus PCSK9 under physiological conditions of pH, ionic strength, and temperature.

TABLE 2

Binding Kinetics and Affinity of the PCSK9 antibody of Example 1 to Human, Cynomolgus Monkey, Mouse, Rat and Rabbit PCSK9

| Antigen | $K_{on}$ Avg ± SD M$^{-1}$s$^{-1}$ (10$^5$) | $K_{off}$ Avg ± SD s$^{-1}$ (10$^{-3}$) | $K_D$ Avg ± SD nM | n |
|---|---|---|---|---|
| Human PCSK9* | 1.2 ± 0.46 | 1.2 ± 0.18 | 11 ± 2.9 | 6 |
| Cyno PCSK9* | 1.1 ± 0.51 | 2.5 ± 0.79 | 25 ± 6.8 | 4 |
| Mouse PCSK9** | NB | NB | NB | 3 |
| Rat PCSK9** | NB | NB | NB | 2 |
| Rabbit PCSK9** | NB | NB | NB | 3 |

"NB" No binding detected;
*Assay performed at 37° C.;
**Assay performed at 25° C.

EXAMPLE 5

Inhibition of PCSK9 Binding to LDL Receptor

PCSK9 regulates plasma LDL-C by reducing LDLR content of the liver and thereby reducing LDL uptake by hepatocytes. The catalytic domain of PCSK9 is the site which binds to the LDLR. Thus, antibodies which recognize the catalytic domain of PCSK9 are expected to inhibit the binding of PCSK9 to the LDLR.

An AlphaLISA® format is used to determine the effect of a test PCSK9 antibody on PCSK9 binding to the LDL receptor. Recombinant full length PCSK9 used in the assay is expressed as a C-terminal HIS-tagged protein in a human embryonic kidney (HEK) 293 stable cell line (Qian et al., J. Lipid Res. 48: 1488-1498, 2007). Recombinant LDL receptor extracellular domain is expressed as a C-terminal FLAG-tagged protein in transiently transfected HEK 293E cells (Qian et al., J. Lipid Res. 48: 1488-1498, 2007). A murine anti-PCSK9 Mab which binds to the C-terminal domain of human PCSK9 is expressed in HEK293 cells and purified over Protein-G affinity column followed by Superdex 200. Monoclonal ANTI-FLAG® BioM2 antibody (Sigma) is a purified mouse IgG1 monoclonal antibody that is covalently attached to biotin by hydrazide linkage. ANTI-FLAG BioM2 will recognize the FLAG sequence at the N-terminus, Met-N-terminus or C-terminus of FLAG fusion proteins. ANTI-FLAG BioM2 can be detected by avidin or streptavidin conjugates. Monoclonal ANTI-FLAG BioM2-Biotin is supplied in 50% glycerol, 10 mM sodium phosphate, pH 7.25, 150 mM NaCl containing 0.02% sodium azide, and stored at −20° C.

AlphaLISA® experiments are conducted in 384-well white proxiplates (Perkin Elmer) using 25 mM HEPES; pH 7.5, 100 mM NaCl, 2.5 mM CaCl2, 0.5% TX-100, 0.1% Casein, 1 mg/ml Dextran-500, and 0.05% Proclin-300 as buffer. The assay uses AlphaLISA® Streptavidin Donor Beads (Perkin Elmer) and the murine anti-PCSK9 Mab conjugated to AlphaLISA® Acceptor beads. When the beads are brought into close proximity via interaction of the binding partners, PCSK9 and LDLR, singlet oxygen is transferred from the donor bead to the acceptor bead. Upon laser excitation at 680 nm, the singlet oxygen excites the acceptor bead to emit light. The acceptor beads are linked to the murine anti-PCSK9 Mab by reductive amination using NaBH$_3$CN (Sigma) and stored at 4° C. The murine anti-PCSK9 Mab-conjugated acceptor beads (22 µg/ml) are preloaded with 2.22 nM PCSK9 for one hr. The donor beads (44 µg/ml) are preloaded with 5.55 nM ANTI-FLAG® BioM2 and 2.22 nM of FLAG-tagged LDLR for one hr. After preloading, 2 µl of the test PCSK9 antibody or control IgG are added to a proxiplate containing 9 µl of each bead mixture (final concentration of PCSK9 and LDLR=1 nM) using a fully automated Multimek (Beckman), and allowed to bind overnight at room temperature. The AlphaLISA® signal (counts per second) are measured on the Envision Turbo (Perkin Elmer). All experiments with the AlphaLISA® assay are conducted under low light conditions.

Following procedures substantially as described above, the binding of human PCSK9 to the LDLR in the AlphaLISA® assay increased as a function of PCSK9 concentration. The addition of the engineered PCSK9 antibody of Example 1 (test PCSK9 antibody) caused a concentration-related and complete inhibition of PCSK9 binding to LDLR, with an average IC50 of about 90 pM. The control IgG4 had no effect in the assay. The results of this assay demonstrate that the engineered PCSK9 antibody of Example 1 inhibits binding of human PCSK9 to the LDLR.

EXAMPLE 6

Inhibition of PCSK9 Function on HepG2 Cells

To determine the effect of a test PCSK9 antibody on the density of LDLR on hepatocytes, human HepG2 cells are cultured in poly-D-lysine coated T75 flasks. After 24 hours, cells are seeded at 5,000 cells per well in 100 ul of DMEM/F-12 (3:1) medium containing 5% (v/v) human lipoprotein depleted serum (LPDS; Intracel) in poly-D-lysine coated 96 well black plates (Becton-Dickinson). After overnight incubation in LPDS-containing medium, cells are incubated with 69 nM (5 ug/mL) C-terminal HIS-tagged recombinant human PCSK9 and a test PCSK9 antibody or an IgG4 control antibody at concentrations ranging from 2.6 to 1333 nM for 2 hours. All incubations are carried out at 37° C. LDLR levels are monitored with an LDLR antibody (Progen) fluorescently labeled with Zenon® Alexa Fluor® 488 Mouse IgG2b Labeling Kit (Invitrogen). The cells are incubated with the detection antibody for 90 min at room temperature and then fixed for 10 min using a formalin-free fixative (Prefer; ANATECH, Ltd) with subsequent permeablization in 0.01% Triton X-100. The cells are stained with 10 ug/ml of propidium iodide (Invitrogen) to determine total cell number. The LDLR signal is quantitated using an Acumen Explorer™ laser-scanning fluorescence microplate cytometer fluorescence detector (TTP LabTech).

Following procedures substantially as described above, human PCSK9 causes a concentration-dependent reduction of LDLR on HepG2 cells, with an EC50 of 18 nM. The engineered PCSK9 antibody of Example 1 (test PCSK9 antibody) inhibited PCSK9-induced suppression of LDLR on HepG2 cells with an IC50 of 104 nM. The human IgG4 control was relatively inactive at concentrations up to 1333 nM. These data demonstrate that the engineered PCSK9 antibody of Example 1 inhibits PCSK9-mediated LDLR degradation.

EXAMPLE 7

Inhibition of PCSK9-Induced Reduction of LDL Uptake

To determine the effect of a test PCSK9 antibody on LDL uptake, HepG2 cells are seeded at 5,000 cells per well in 100 ul of DMEM/F-12 (3:1) medium supplemented with 5% human LPDS on poly-D-lysine coated 96-well black plates and incubated at 37° C. in an atmosphere of 5% $CO_2$ for 18 hours. Human PCSK9 (69 nM) is added to the cells with or without a PCSK9 test antibody or a human IgG4 control at concentrations ranging from 2.6 nM to 1333 nM and pre-incubated with cells for 2 hr at 37° C. Following the addition of 100 ng/well of fluorescently-labeled LDL (BODIPY-LDL, Invitrogen), the cells are then incubated for 4 hr at 37° C. Cells are fixed in a formalin-free fixative (Prefer; ANATECH, Ltd.) for 20 min at room temperature. After washing cells twice with PBS, cells are permeablized with PBS buffer containing 0.01% Triton X-100 for 15 min at room temperature and stained with 10 ug/mL of propidium iodide to determine total cell number. LDL uptake is determined using an Acumen Explorer™ laser-scanning fluorescence microplate cytometer and expressed as a percentage of fluorescent cells relative to total cells. The response to test PCSK9 antibody or control IgG is expressed as percentage inhibition of PCSK9, i.e., the percent return to maximum LDL uptake in the absence of PCSK9 relative to baseline LDL-C uptake in the presence of PCSK9 alone. Corresponding IC50 values for inhibition of PCSK9-induced reduction of LDL uptake are also calculated.

Following procedures substantially as described above, human PCSK9 caused a concentration-related reduction of LDL uptake in HepG2 cells with an EC50 of 32 nM. The engineered PCSK9 antibody of Example 1 reversed the PCSK9-induced inhibition, reflected as increased LDL uptake, whereas the control IgG did not reverse the inhibition. Specifically, the engineered PCSK9 antibody of Example 1 demonstrated a mean maximum percent inhibition of PCSK9 of 84% and an average IC50 of 194 nM. These data demonstrate that the engineered PCSK9 antibody of Example 1 inhibits PCSK9-induced reduction of LDL uptake.

EXAMPLE 8

In vivo Efficacy

To determine the in vivo pharmacokinetic (PK) and/or pharmacodynamic (PD) effects of a test PCSK9 antibody, the test antibody may be administered to normal cynomolgus monkeys and various PK and/or PD parameters subsequently determined. For example, a test PCSK9 antibody may be administered intravenously or subcutaneously to healthy, naive cynomolgus monkeys and serum concentrations of the test antibody may then be measured by use of a human IgG sandwich ELISA. Serum concentrations taken over various timepoints after antibody administration may be used to determine various PK parameters of the test antibody, including T1/2, $C_{max}$, AUC and plasma clearance (CL). Similarly, a test PCSK9 antibody may be administered intravenously or subcutaneously to healthy, naive cynomolgus monkeys and serum concentrations of LDL-C may be measured by autoanalyzer (Direct LDL-C Plus, $2^{nd}$ Gen., Roche Diagnostics).

Following procedures substantially as described above, the pharmacokinetics of the engineered PCSK9 antibody of Example 1 was evaluated in healthy cynomolgus monkeys following single dose intravenous administrations of 1, 5 or 15 mg/kg, and after a single subcutaneous dose of 5 mg/kg. Pharmacokinetic parameters determined from these studies are provided in Table 3, below.

TABLE 3

Pharmacokinetic parameters for the engineered PCSK9
antibody of Example 1 in cynomolgus monkeys.

Intravenous (n = 4/group)

| Dose (mg/kg) | $T_{1/2}$ (d) | $C_{max}$ (µg/mL) | $AUC_{total}$ (hr*µg/mL) | CL (mL/hr/kg) |
|---|---|---|---|---|
| 1 | 5.4 ± 1.0 | 19.8 ± 1.1 | 2218 ± 222 | 0.45 ± 0.04 |
| 5 | 7.3 ± 1.3 | 107.3 ± 3.2 | 14378 ± 1374 | 0.35 ± 0.04 |
| 15 | 8.4 ± 3.0 | 260.3 ± 45.0 | 57290 ± 16535 | 0.28 ± 0.07 |

Subcutaneous (n = 3/group)

| Dose (mg/kg) | $T_{max}$ (days) | $C_{max}$ (µg/mL) | $T_{1/2}$ (d) | $AUC_{total}$ (hr*µg/mL) | CL/F (mL/hr/kg) | % F |
|---|---|---|---|---|---|---|
| 5 | 2.7 ± 0.6 | 32.4 ± 1.9 | 5.4 ± 0.7 | 11575 ± 1345 | 0.44 ± 0.05 | 81 |

Serum LDL was measured following administration of the engineered PCSK9 antibody of Example 1 in two independent studies. In both studies, evidence of LDL-C suppression was apparent by 24 hours post-administration with the engineered PCSK9 antibody of Example 1. After intravenous (i.v.) administration of the antibody of Example 1 at 5 mg/kg, a maximal mean LDL-C decrease of 60% (Study 1) and 25% (Study 2) was observed. At 5 mg/kg i.v., mean LDL-C suppression was maintained for approximately 8-weeks (Study 1) and 2-weeks (Study 2). In Study 2, there was a modest effect of dose (1 to 15 mg/kg) on the magnitude of LDL-C suppression (25 to 35%). The effect of dose on duration of LDL-C suppression was more evident. When administered subcutaneously (5 mg/kg), the engineered antibody of Example 1 was effective in suppressing LDL-C levels to a magnitude similar to that observed after intravenous dosing. There was no effect on serum high density lipoprotein cholesterol following administration of any dose of the engineered antibody of Example 1.

EXAMPLE 9

Physical-Chemical Properties of Engineered PCSK9 Antibody

The engineered PCSK9 antibody of Example 1 was also found to have good solubility, chemical stability, and physical stability.

A. Solubility

Sufficiently high solubility is desired to enable convenient dosing. For example, a 1 mg/kg dose administered by a 1.0 mL injection into a 100 kg patient will require solubility of 100 mg/mL. In addition, maintaining the antibody in a monomeric state without high molecular weight (HMW) aggregation at high concentration is also desirable. To determine solubility of a test antibody, the antibody may be dialyzed into (1) 10 mM citrate pH6; (2) 10 mM citrate pH6, 150 mM NaCl; and (3) phosphate buffered saline (PBS) pH7.4. Recovered dialysate may then be analyzed by analytical size exclusion chromatography (SEC) to measure percent HMW. Test antibody may then be concentrated in a 4 mL centrifugal concentrator at ~25 C until solubility limit is reached or void volume of the concentrator is reached. If void volume is reached, concentration is reported as >. Concentrated antibody may then be analyzed by SEC to measure percent HMW. To determine if any increase in % HMW upon concentration is reversible, the concentrated sample may be diluted to 1 mg/mL and analyzed by SEC.

Following procedures substantially as described above, the engineered PCSK9 antibody of Example 1 displayed a solubility of greater than 128 mg/mL under all conditions tested. In addition, only low levels of HMW were present at high concentration.

TABLE 4

Percent HMW of Solubility Samples determined by SEC

| | % HMW (Dialysate) | % HMW (Concentrate) | % HMW (1 mg/mL dilution) |
|---|---|---|---|
| 10 mM Citrate, pH6 | 0.75% | 1.60% | 0.93% |
| 10 mM Citrate, 150 mM NaCl, pH6 | 0.62% | 1.39% | 0.90% |
| PBS, pH7.4 | 0.94% | 2.00% | 1.34% |

B. Chemical Stability

Chemical stability facilitates the development of drug formulations with sufficient shelf-life. To assess the chemical stability of a test antibody, the antibody may be formulated at a concentration of 1 mg/mL in 10 mM citrate buffered at pH4, pH5, pH6, or pH7. The formulated samples are then incubated for 4 weeks at 4° C., 25° C., and 40° C. in an accelerated degradation study. Changes in the charge profile of the antibody, reflecting chemical changes, may be assessed using capillary isoelectric focusing (cIEF) according to standard procedures. Following procedures substantially as described above, an analysis of the chemical stability of the engineered antibody of Example 1 provided the following results.

TABLE 5

Chemical stability determined by cIEF

| | Change in % main peak after 4 weeks (relative to 4° C.) | |
|---|---|---|
| | (25° C. storage) | (40° C. storage) |
| 10 mM Citrate, pH5 | −0.4 | NT |
| 10 mM Citrate, pH6 | −4.1 | −24.7 |
| 10 mM Citrate, pH7 | −7.7 | NT |

The results demonstrate that after 4 weeks storage at 25° C., the % main peak decreases by only 4.1 percentage points when formulated at pH6 (a common pH used in antibody formulation), indicating that the engineered PCSK9 antibody of Example 1 has sufficient chemical stability to facilitate the development of solution formulations with adequate shelf-life. Furthermore, the antibody also displays good chemical stability at pH5 and, to a lesser extent pH7, indicating that the antibody has stability characteristics that may permit formulation over a range of pH units.

C. Physical Stability

To assess the physical stability of a test antibody, the antibody may be formulated at a protein concentration of 1 mg/mL in 10 mM citrate buffered at pH4, pH5, pH6, or pH7 (or 10 mM Tris, pH 8). The samples are then incubated for 4 weeks at 4° C., 25° C., and 40° C. in an accelerated degradation study. Following the incubations, physical stability is assessed using size exclusion chromatography (SEC), which separates the desired monomeric antibody from aggregated high molecular weight (HMW) antibody.

Table 6 summarizes the results of an analysis of the physical stability of the engineered PCSK9 antibody of Example 1, following procedures substantially as described above. The data shows that at pH5, pH6, and pH7, the change in HMW over 4 weeks at 25° C. or 40° C. was less than 1% indicating that this antibody has good physical stability and is resistant to self-association and aggregation.

TABLE 6

Percent HMW of Physical Stability Samples

| | % HMW determined by SEC | | | | |
|---|---|---|---|---|---|
| | pH4 | pH5 | pH6 | pH7 | pH8 |
| Initial Sample | 0.26 | 0.32 | 0.40 | 0.50 | 1.31 |
| 25 C. for 4 weeks | 0.37 | 0.44 | 0.51 | 0.66 | 2.10 |
| 40 C. for 4 weeks | 20.34 | 1.15 | 1.02 | 1.32 | 3.41 |

We claim:

1. An antibody, or antigen-binding fragment thereof, comprising a heavy chain variable region (HCVR) and a light chain variable region (LCVR), wherein the HCVR comprises the complementarity determining regions (CDRs) HCDR1, HCDR2 and HCDR3 and the LCVR comprises the CDRs LCDR1, LCDR2 and LCDR3, wherein the amino acid sequence of HCDR1 is given by SEQ ID NO: 1, the amino acid sequence of HCDR2 is given by SEQ ID NO: 2, the amino acid sequence of HCDR3 is given by SEQ ID NO: 3, the amino acid sequence of LCDR1 is given by SEQ ID NO: 4, the amino acid sequence of LCDR2 is given by SEQ ID NO: 5, and the amino acid sequence of LCDR3 is given by SEQ ID NO: 6, wherein said antibody, or antigen binding fragment thereof, binds to human PCSK9.

2. The antibody or antigen-binding fragment of claim 1, comprising a heavy chain variable region (HCVR) and a light chain variable region (LCVR), wherein the amino acid sequence of the HCVR is given by SEQ ID NO: 7 and the amino acid sequence of the LCVR is given by SEQ ID NO: 8.

3. The antibody or antigen-binding fragment of claim 2, comprising two HCVRs and two LCVRs wherein the amino acid sequence of each HCVR is given by SEQ ID NO: 7, and the amino acid sequence of each LCVR is given by SEQ ID NO: 8.

4. A method of treating hyperlipidemia or hypercholesterolemia comprising administering to a patient in need thereof an effective amount of an antibody or antigenbinding fragment of claim 1.

5. A pharmaceutical composition comprising an antibody or antigen-binding fragment of claim 1 and one or more pharmaceutically acceptable carriers, diluents or excipients.

6. The pharmaceutical composition according to claim 5 comprising an antibody comprising two heavy chains (HCs) and two light chains (LCs) wherein the amino acid sequence of each HC is given by SEQ ID NO: 9, and the amino acid sequence of each LC is given by SEQ ID NO: 10.

7. An antibody comprising two HCVRs and two LCVRs wherein the amino acid sequence of each HCVR is given by SEQ ID NO: 7, and the amino acid sequence of each LCVR is given by SEQ ID NO: 8.

8. An antibody comprising a heavy chain (HC) and a light chain (LC), wherein the amino acid sequence of the HC is given by SEQ ID NO: 9, and the amino acid sequence of the LC is given by SEQ ID NO: 10.

9. An antibody comprising two heavy chains (HCs) and two light chains (LCs) wherein the amino acid sequence of each HC is given by SEQ ID NO: 9, and the amino acid sequence of each LC is given by SEQ ID NO: 10.

10. A method of treating hyperlipidemia or hypercholesterolemia comprising administering to a patient in need thereof an effective amount of the antibody of claim 9.

11. An antibody consisting of two heavy chains and two light chains, wherein the amino acid sequence of each heavy chain is given by SEQ ID NO: 9, and the amino acid sequence of each light chain is given by SEQ ID NO: 10.

* * * * *